United States Patent
Lam et al.

(10) Patent No.: US 10,168,341 B2
(45) Date of Patent: Jan. 1, 2019

(54) DEVICES FOR DETERMINING CELL FORCE PROPERTIES AND METHODS OF MANUFACTURING THE DEVICES

(71) Applicants: EMORY UNIVERSITY, Atlanta, GA (US); CHILDREN'S HEALTHCARE OF ATLANTA, INC., Atlanta, GA (US)

(72) Inventors: Wilbur A. Lam, Decatur, GA (US); David Myers, Atlanta, GA (US); Yongzhi Qiu, Atlanta, GA (US)

(73) Assignees: Emory University, Atlanta; Children's Healthcare of Atlanta, Inc., Atlanta, GA (US)

( * ) Notice: Subject to any disclaimer, the term of this patent is extended or adjusted under 35 U.S.C. 154(b) by 0 days.

(21) Appl. No.: 14/202,946

(22) Filed: Mar. 10, 2014

(65) Prior Publication Data

US 2014/0256033 A1    Sep. 11, 2014

Related U.S. Application Data

(60) Provisional application No. 61/775,136, filed on Mar. 8, 2013.

(51) Int. Cl.
*G01N 21/75* (2006.01)
*B01L 3/00* (2006.01)
(Continued)

(52) U.S. Cl.
CPC ............ *G01N 33/86* (2013.01); *B01L 3/5027* (2013.01)

(58) Field of Classification Search
CPC . G01N 33/86; B01L 3/5027; B01L 2300/069; B01L 2300/0816;
(Continued)

(56) References Cited

U.S. PATENT DOCUMENTS

| 6,013,513 A * | 1/2000 | Reber | B01L 3/5027 422/504 |
| 7,223,363 B2 * | 5/2007 | McNeely | B01F 5/10 422/417 |

(Continued)

FOREIGN PATENT DOCUMENTS

WO    WO 2010/102335 A1    9/2010

OTHER PUBLICATIONS

Lam et al., "Mechanics and contraction dynamics of single platelets and implications for clot stiffening," Nat Mater, 2011, 10(1): 61-66.
(Continued)

*Primary Examiner* — Dean Kwak
(74) *Attorney, Agent, or Firm* — Emory Patent Group

(57) ABSTRACT

A device may be configured to allow individual measuring of at least one property of at least one cell, such as measuring a contraction force of a platelet. The device may include a plurality of wells. Each well may include a hydrogel layer, the hydrogel layer including a hydrogel having a top surface that includes a pattern of cell interaction regions. The wells may differ in stiffness properties of the hydrogel and/or biochemical conditions. Each cell interaction region may include a group of at least two cell interaction sites. The spacing between each cell interaction region may be greater than a spacing between the at least two cell interaction sites of each cell interaction region. In this way, cell-cell interactions may be reduced and thereby increasing number of individual cells capable of being measured.

11 Claims, 6 Drawing Sheets

(51) Int. Cl.
*G01N 33/86* (2006.01)
*G01N 21/77* (2006.01)

(58) Field of Classification Search
CPC ....... B01L 2300/0874; B01L 2300/088; B01L 2400/0487; B01L 3/502707; B01L 3/502746
USPC ................ 422/500–503, 401, 407, 425, 426; 436/170
See application file for complete search history.

(56) References Cited

U.S. PATENT DOCUMENTS

| | | | | |
|---|---|---|---|---|
| 2003/0040129 | A1* | 2/2003 | Shah | B01L 3/5027 506/32 |
| 2003/0113925 | A1* | 6/2003 | Gordon et al. | 436/10 |
| 2003/0224457 | A1* | 12/2003 | Hurt | G01N 33/80 435/7.2 |
| 2005/0009101 | A1* | 1/2005 | Blackburn | B01L 3/5027 435/7.1 |
| 2007/0026416 | A1* | 2/2007 | Fuchs | B01L 3/502746 435/6.16 |
| 2007/0231851 | A1* | 10/2007 | Toner | B01L 3/502746 435/29 |
| 2009/0272657 | A1* | 11/2009 | Bhatia | B01L 3/502715 205/792 |
| 2012/0058500 | A1 | 3/2012 | Mitchell et al. | |
| 2013/0083311 | A1 | 4/2013 | Li et al. | |
| 2013/0096029 | A1* | 4/2013 | Sia | C12Q 1/025 506/10 |
| 2014/0085457 | A1* | 3/2014 | Staker | G01N 21/6456 348/95 |
| 2015/0056643 | A1 | 2/2015 | Sniadecki et al. | |
| 2015/0226741 | A1* | 8/2015 | Liu | G01N 33/574 435/7.24 |

OTHER PUBLICATIONS

Polio et al., "A micropatterning and image processing approach to simplify measurement of cellular traction forces," Acta biomaterialia, 2012, 8(1): 82-88.

Ting et al., "A Microfluidic Device for Platelet Aggregate Force Measurement," 9th Annual Northwest 2012 Biomechanics Symposium, 2012, retrieved from the Internet <URL:http://biomechanics.uoregon.edu/nwbs2012/ALL%20ABSTRACTS/Podium1-4.pdf> on Aug. 10, 2015.

* cited by examiner

DEVICES FOR DETERMINING CELL FORCE PROPERTIES AND METHODS OF MANUFACTURING THE DEVICES

GOVERNMENT ACKNOWLEDGMENT

This invention was made with government support under Grant CBET1150235 awarded by the National Science Foundation. The government has certain rights in the invention.

CROSS-REFERENCE TO RELATED APPLICATION

This application is a non-provisional of Application Ser. No. 61/775,136, filed Mar. 8, 2013, which is hereby incorporated by this reference in its entirety.

BACKGROUND

While much is known regarding the chemical pathways involved in platelet activation and clot formation, little is generally known about the physical and mechanical interactions between platelets and fibrin. During clot formation, activated platelets from the blood attach to and interact with fibrin polymers that form; physically, the platelets contract against the fibrin scaffolds. This contraction by platelets changes the mechanical properties of the clot itself. Mechanical changes in the clot are believed to underlie some of the pathophysiology of thrombotic conditions such as cardiovascular disease and stroke. However, current methods generally only allow for the measurement of large scale, bulk clot retraction, obscuring the actually behavior of the individual or small numbers of platelets during clot formation.

SUMMARY

There is a need for a device capable of being used to determine at least one force property of at least one cell, such as contraction force of at least one platelet.

In some embodiments, the disclosure relates to devices for measuring at least one property of at least one cell. In some embodiments, the device may include least one well; and a hydrogel layer disposed in the at least one well, the hydrogel layer including a hydrogel having a top surface that includes a pattern of cell interaction regions. In some embodiments, each cell interaction region may include a group of at least two cell interaction sites. In some embodiments, a spacing between each cell interaction region may be greater than a spacing between the at least two cell interaction sites of each cell interaction region.

In some embodiments, the device may a plurality of wells. In some embodiments, each well may include a hydrogel layer, the hydrogel layer including a hydrogel having a top surface that includes a pattern of cell interaction regions. In some embodiments, each cell interaction region may include a group of at least two cell interaction site. In some embodiments, a spacing between each cell interaction region that may be greater than a spacing between the at least two cell interaction sites of each cell interaction region. In some embodiments, the wells may include a different biochemical condition and/or hydrogel layer.

In some embodiments, each well may include a different hydrogel, a different pattern of cell interaction regions, a different biochemical solution, or a combination thereof. In some embodiments, each well may include a hydrogel with a different stiffness. In some embodiments, each well may include a different hydrogel, each hydrogel having a different ratio of acrylamide to bis-acrylamide.

In some embodiments, the disclosure relates to methods of manufacturing a device for measuring at least one property of at least one cell. In some embodiments, the method may include forming a hydrogel layer in a layer, the hydrogel layer including a hydrogel and a pattern of cell interaction regions disposed on the top surface of the hydrogel. In some embodiments, the forming may include disposing a coverslip with the pattern of cell interaction regions onto the layer, the layer including a plurality of channels; injecting a solution into each channel of the layer, the solution including a polyacrylamide solution; polymerizing the hydrogel; and discarding the coverslip.

Additional advantages of the disclosure will be series forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DESCRIPTION OF FIGURES

The disclosure can be better understood with the reference to the following drawings and description. The components in the figures are not necessarily to scale, emphasis being placed upon illustrating the principles of the disclosure.

DESCRIPTION OF EMBODIMENTS

Figure 1A:
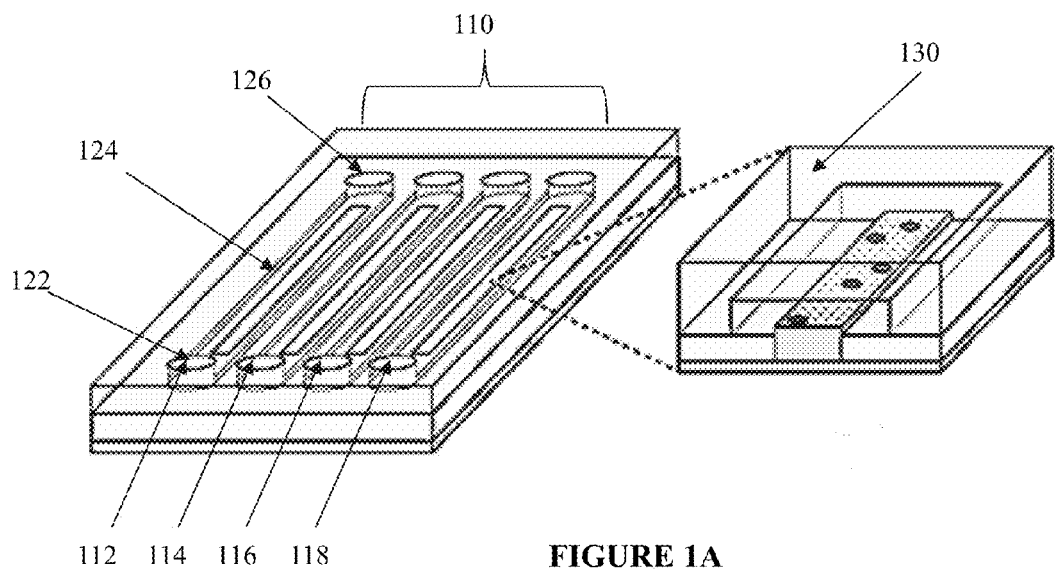
FIG. 1A shows a device according to embodiments.

The following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

In various embodiments, the devices and systems may be configured to individually determine at least one property of at least one cell, such as at least one force property. In some embodiments, the at least one property may include and is not limited to contractile force, fluidic force, as well as other parameters may be also be determined. The cell may include but is not limited to heart muscle cells, skeletal cells, blood platelets, as well as other cells that contract and/or capable of generating force.

The devices and systems address the above-described deficiencies of current methods. The devices can individually measure at least one property, for example, contraction force of at least one cell because the devices can reduce cell-cell interactions by the disclosed pattern of cell interaction regions (e.g., fibrinogen dots). The devices according to embodiments can also reduce manufacturing complexity by enabling large tolerances in alignment between different device layers (hydrogel, protein, and fluidic). The microfluidic nature can also enable extremely small patient samples to be used for each measurement, as little as 100 uL of whole blood should be sufficient for a test. The device can also be compatible with confocal microscopy for high resolution and live-cell imaging.

It is to be further understood that the devices and systems according to embodiments may be configured or adjusted according to type or property of cell(s) (e.g., size, shape, deformability, and surface characteristics). The devices and systems may also alternatively or additionally be configured or adjusted according to the biochemical condition (e.g., concentration of thrombin and/or ADP) and/or stiffness of hydrogel.

In some embodiments, the devices may be sterilized. In further embodiments, the devices may be a single, use device. In further embodiments, the devices may be disposable.

As shown in FIG. 1A, a device 100 may include at least one well 110 extending substantially along the length of the device. The well may be configured to receive a sample for analyzing. The sample may include but is not limited to a biological and/or prepared sample that includes the cells, such as but not limited to washed platelets, blood or blood components. In some embodiments, the sample may also include biochemical solution (e.g., an agonist). The device may include any number of wells. Although FIG. 1A shows four wells 112, 114, 116, 118, it is to be understood that the device may include more or less wells.

Figure 1B:
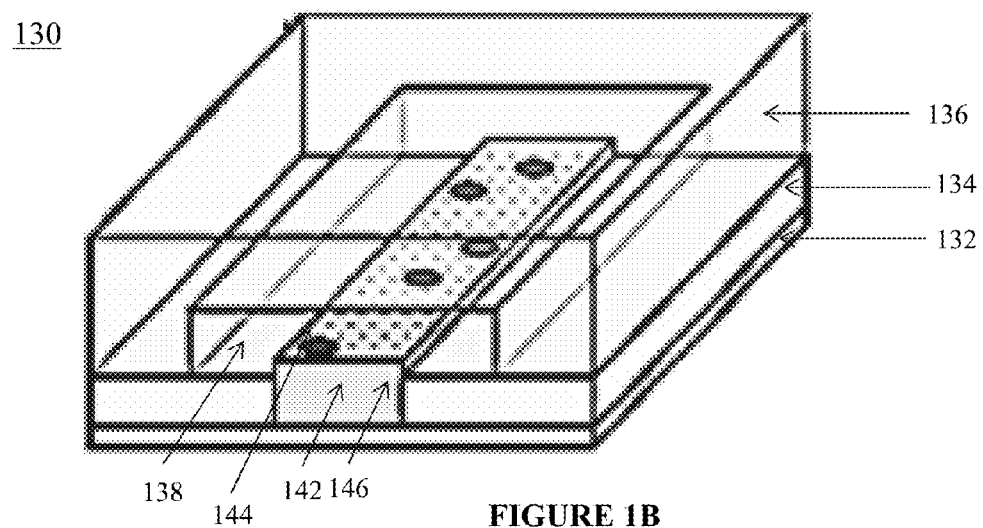
FIG. 1B shows a partial cross-sectional view of the device of FIG. 1.

In some embodiments, each well 110 may include an input 122 for the sample and/or a solution (e.g., storage and/or biochemical solution) and an outlet 126. In some embodiments, each well 110 may also include a channel 124 extending between the input 122 and the outlet 126. A cross-section 130 of a channel 124 of a well 110 is shown in FIG. 1B. In some embodiments, the outlet 126 may be configured to remove excess sample and/or solution. In some embodiments, the outlet 126 may be configured to be connected to a pressure source (e.g., a vacuum to remove the solution).

In some embodiments, the inlet 122 and/or the outlet 126 may be configured for a microfluidic system. For example, a microfluidic system may include a syringe, syringe pump, and tubing. In other embodiments, the microfluidic system may include alternative and/or additional components.

In some embodiments, the device, e.g., the inlet 122 and/or the outlet 126 may have any size. In some embodiments, the size of the inlet and/or outlet may be dependent on the delivery system used to deliver the sample. For example, the inlet 122 and/or the outlet 126 may be sized such that the inlet 122 and/or the outlet 126 are configured to grip the tubing of a microfluidic system.

In some embodiments, each well 110 of the device may include a hydrogel layer 142 that extends along the length of the channel 124. In some embodiments, the hydrogel layer 142 may extend substantially along or partially along the length of the channel 124. In some embodiments, the hydrogel layer 142 may be any kind of hydrogel. In some embodiments, the hydrogel layer 142 may be a polyacrylamide hydrogel.

In some embodiments, the plurality of wells 110 may include the same hydrogel layer, different hydrogel layer, or a combination thereof. In some embodiments, the hydrogel layer may differ in stiffness. For example, the hydrogel layer for each well may be a polyacrylamide hydrogel having a different ratio of acrylamide to bis-acrylamide. In some embodiments, the hydrogel layer may have a stiffness from about 1-100 kPa. In some embodiments, the stiffness may be in a different range, for example, above 100 kPa.

Figure 2A:
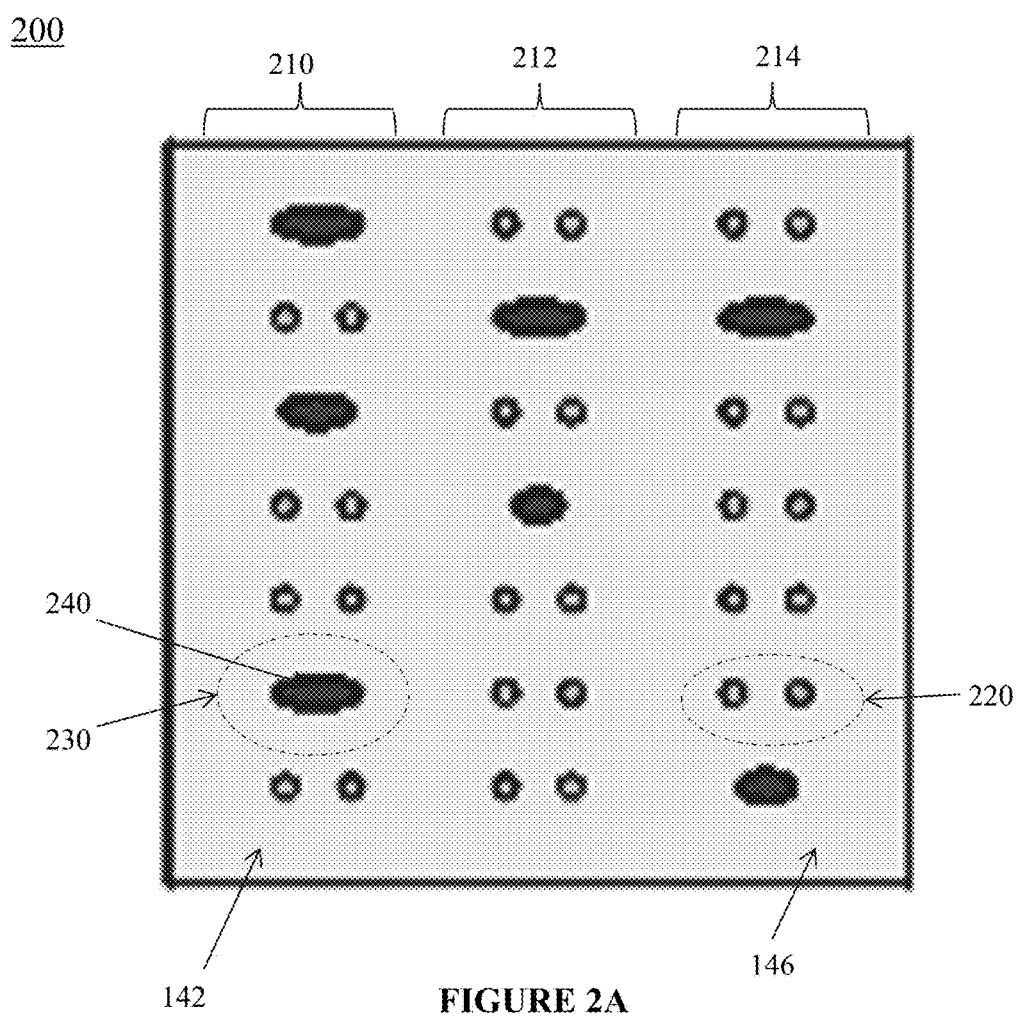
FIG. 2A-2C shows another partial enlarged view of a hydrogel layer of the device of FIG. 1.

In some embodiments, the hydrogel layer 142 may include a pattern of cell interaction regions 144 on the top surface of a hydrogel 146. In some embodiments, the pattern may be an array of cell interaction regions, for example, as shown in the enlarged view 200 of a top surface of the hydrogel 142 in FIGS. 2A-2C. In some embodiments, the cell interaction regions may be disposed in substantially evenly spaced columns. There may be any number of columns. Although FIG. 2A shows three spaced columns 210, 212, and 214 of the cell interaction regions, it is to be understood that the device may include more or less columns of cell interaction regions. In some embodiments, the cell interaction regions may be disposed in a different pattern. For example, the spacing between columns of cell interaction regions may vary. In some embodiments, the plurality of wells may include the same pattern of cell interaction regions, a different pattern of cell interaction regions, or a combination thereof.

As shown in FIG. 2A, a cell interaction region 220 may include a group of cell interaction sites. In some embodiments, the cell interaction sites may be made of a protein. In some embodiments, the cell interaction sites may be made of fibrinogen.

In some embodiments, the group may include two cell interaction sites. In other embodiments, the group may include more than two cell interaction sites. For example, the group may include two, three, four, etc.

In some embodiments, the cell interaction sites of a group may include a single row of cell interaction sites. In other embodiments, the cell interaction sites of a group may be disposed in more than one row of cell interaction sites. For example, a group of cell interaction sites may include two or more rows of cell interaction sites (e.g., 2X2, 2X3, 3X3, etc.).

In some embodiments, each cell interaction region of the pattern may be the same, different, or a combination thereof. In some embodiments, the cell interaction region may include a different number, different shape, different spacing, different size of cell interaction sites, among others, or a combination thereof.

In some embodiments, the size of each cell interaction region may be optimized for a single cell, for example, by optimizing the spacing and size of the cell interaction sites. In some embodiments, the size of the interaction region, which may include at least partially the cell interaction sites of that region and the spacing therebetween, may substantially correspond to a size of a cell (e.g., resting cell and/or activated cell). For example, as shown in FIG. 2A, the cell 240 adheres to the cell interaction region 230 that includes two cell interaction cites and thereby the cell interaction region 230 can be optimized for a cell 240.

Figure 2B:
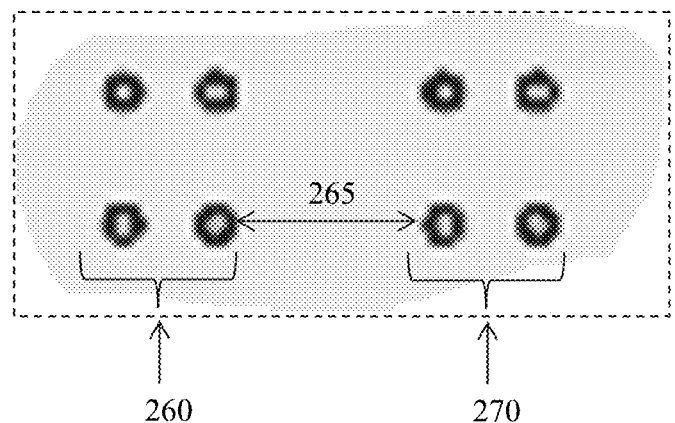
Figure 2C:
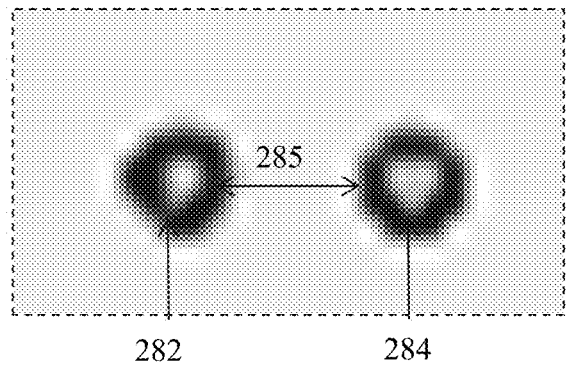

In some embodiments, the spacing or distance between the cell interaction sites of a cell interaction region may be less than the spacing or distance between cell interaction regions. For example, as shown in FIGS. 2B and 2C, spacing or distance 265 between cell interaction regions 260 and 270 may be larger than spacing or distance 285 between cell interaction sites 282 and 284 of a cell interaction region. By way of example, the spacing between the cell interaction regions can thus be larger than a cell to be analyzed. In this way, interactions between cells may be reduced thereby increasing number of individual cells capable of being measured.

In some embodiments, the spacing or distance between sites of a region may substantially correspond to a distance to which at least an activated cell can easily reach. For example, for a platelet, the spacing or distance between sites of a region may be greater than a resting platelet, but the spacing or distance between sites of a region may correspond to a distance that a platelet filipodia (when the platelet is activated may be capable of reaching.

Figure 3:
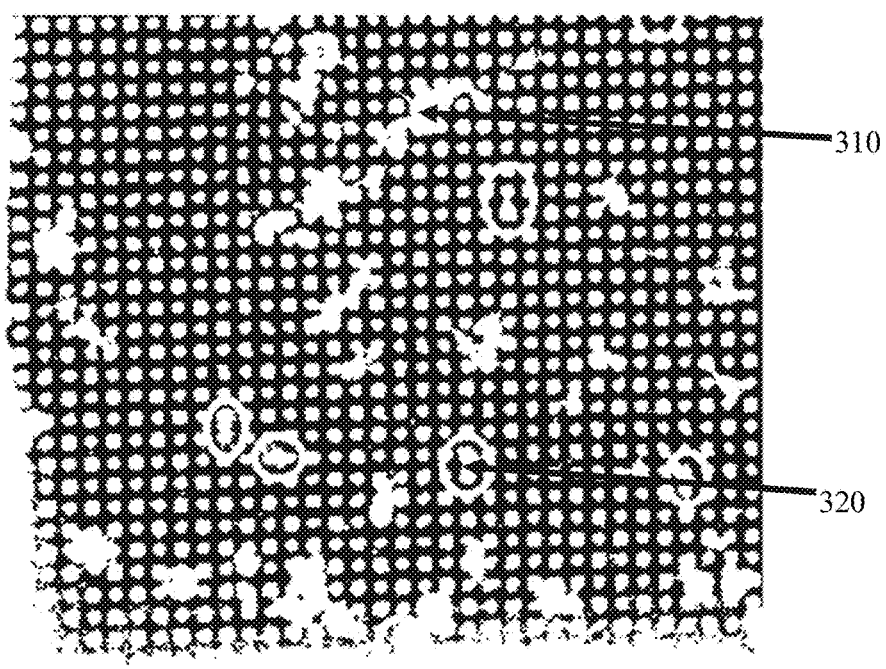
FIG. 3 shows an example of a platelets that interacted with a pattern of fibrinogen dots.

FIG. 3 shows an example 300 of platelet cells placed on a hydrogel with an array of equally spaced protein dots, for example, based in part on Polio S, Rothenberg K, Stamenović D, Smith M. A micropatterning and image processing approach to simplify measurement of cellular traction forces. *Acta Biomaterialia*. 2012;8(8bb30d30-caa9-8de0-0147-81013bde8f34):82-90. This design can result in numerous platelet-to-platelet interactions 310 thus resulting only in a handful of individual platelets 320 to be measured. This pattern also requires significant computational needs to determine properties of a cell. For example, to determine a force property of a cell that lands on the pattern shown in FIG. 3, the original position of each dot generally must be estimated from the moved position. This can result in significant computation because the more dots in the array the more work needed to determine how much each dot has moved. Additionally, the map of the movement of the dots needs to be further analyzed to determine a property.

Figure 4:
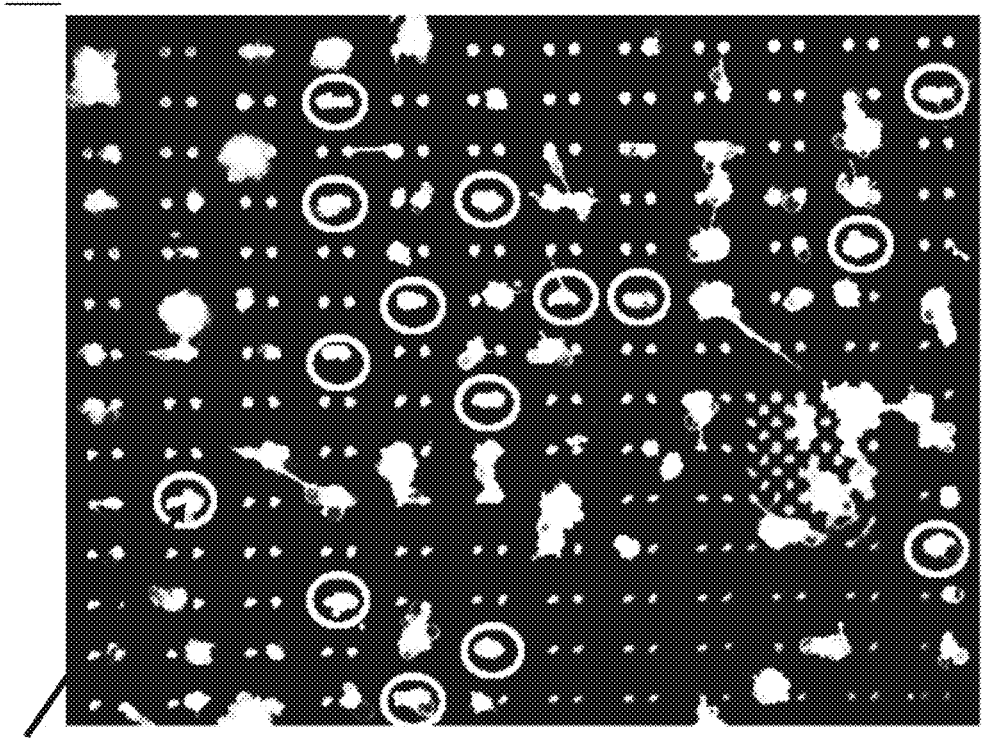
FIG. 4 shows an example of platelets that interacted with a pattern of cell interaction regions according to embodiments.

The pattern of cell isolation regions according to embodiments overcomes these deficiencies. FIG. 4 shows an example 400 of platelet cells placed on a hydrogel layer having a pattern of cell interaction regions on its top surface corresponding to some embodiments shown and described with respect to FIGS. 2A-2C. For example, in operation, the platelets can land on the cell interaction regions and can exert a force that moved the cell interaction sites of the cell interaction region because the substrate is composed of a mechanically compliant material. Because the mechanical properties of the hydrogel are generally well characterized, the force exerted by a single platelet or small aggregate of platelets can be directly proportional to the distance in which a single dot of protein moves. The platelets can also be held over the cell interaction regions using a microfluidic system.

According to embodiments, the pattern of cell interaction regions can increase the number of individual platelets 410 capable of being measured while reducing the number of platelet-platelet interactions. Additionally, the pattern of cell interaction regions according to embodiments can reduce computational needs necessary to determine the at least one force property (e.g., contraction force). For example, the force can be easily determined by measuring the distance between the sites of a cell interaction region that interacted with a cell and the original distance between the sites (e.g., before the sample was applied).

As shown in the cross-section 130 in FIG. 1B, each well 110 may be self-contained. In this way, the wells of the device may include multiple, different biochemical conditions (e.g., agonist and biochemical concentrations) and/or hydrogels. For example, the wells of the device may include a different biochemical condition (e.g., concentration), same biochemical condition, different hydrogel (e.g., hydrogel with different stiffness), same hydrogel, or a combination thereof.

In some embodiments, the device 100 may be constructed to include a plurality of layers. In some embodiments, the device 100 may include a first layer 132, a second layer 134, and a third layer 136. In some embodiments, the device 100 may include a hydrogel layer 142.

In some embodiments, the first layer may be a base layer or substrate. The first layer may be made of a flexible material. For example, the first layer may be made of a glass or plastic material.

The second layer 134 may be disposed above the first layer 132. In some embodiments, the second layer 134 may be made of silicone, such as polydimethylsiloxane (PDMS).

In some embodiments, the hydrogel layer 142 may be disposed in (e.g., in a channel in) the second layer above the first layer. In some embodiments, the hydrogel layer 142 may extend above the top surface of the second layer 134. The second layer 137 may be configured so that each well includes a hydrogel layer.

In some embodiments, the third layer 136 may be made of silicone, such as polydimethylsiloxane (PDMS). The third layer 136 may be above the second layer 134 and the hydrogel layer 142, and may cover the hydrogel layer 142. The third layer 136 may include a section that abuts the second layer 134 and a section that includes sufficient space above the hydrogel layer 142 so as to form a channel 138 that extends between the inlet 122 and the outlet 126. The channel 138 may be disposed above the hydrogel layer 142 and the second layer 134. The third layer 136 may be configured so that each well is self-contained and has a channel 138. The channel may be configured to receive a sample and/or storage solution.

In operation, a sample (e.g., cleaned platelets, blood, or other solution) including a plurality of cells may be placed in a well of the device 100 via the inlet 122. In some embodiments, the sample may be placed in the inlet 122 using a delivery device, such as a syringe or pipette. In some embodiments, the device 100 may be used with a microfluidic system whereby the microfluidic system may be configured to hold the sample over the pattern of cell interaction regions.

In some embodiments, the sample including the cells may also include least one biochemical solution to help facilitate adhesion of the cells to the cell interaction region by activating the cells of the sample. The biochemical solution(s) can cause the biochemical condition in which the cells are caused to interact with the cell interaction regions on which the cells land. In some embodiments, a different solution can be added to each well. Because the substrate is made of mechanically compliant material, the cells can cause a cell interaction site to move when exerting a force (e.g., when activated to contract by a biochemical solution).

After a period of time, the amount of interaction (e.g., the amount of contraction) of an individual cell and/or a plurality of cells can be used to determine at least one property. For example, the contraction force exerted by a cell can be determined from the distance that the sites of the region move from the original position (e.g., difference between the position of the site after the cells contract and the original position of the site). The force exerted by a single cell or a plurality of cells can be directly proportional to the distance for which a cell interaction site moves.

In some embodiments, the sample can be continuously flowed over the pattern of the cell interaction regions in the channels using a microfluidic system (e.g., a syringe, a syringe pump, and tubing can be inserted into the device to deliver the sample). The small channel dimensions can enable tight control of the fluid velocity and direction of the sample, thereby giving excellent control over the applied fluid forces. Cells, for example, platelets, can adhere to the cell interaction regions and contract under flow, and thus can enable a good biophysical recapitulation of the contraction microenviroment, and provide measurements to determine the locally applied forces (e.g., fluidic forces, contraction forces, among others, or a combination thereof).

Figure 5:
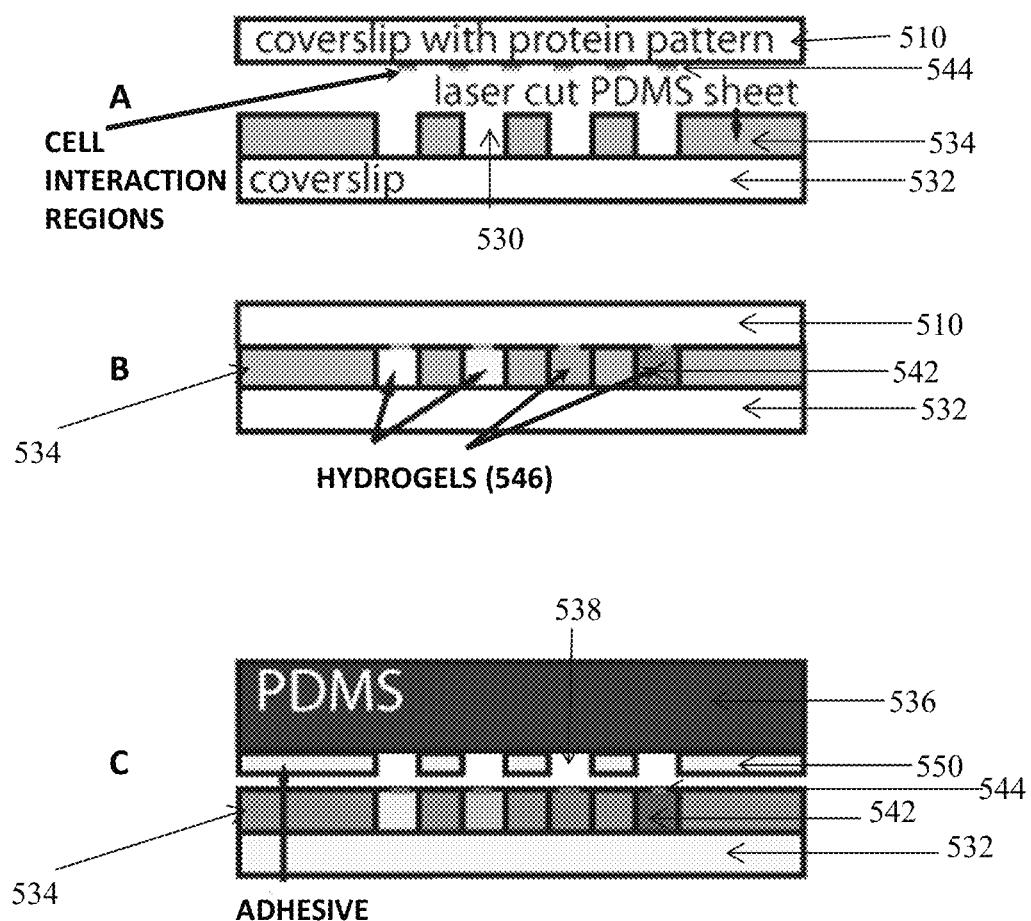
FIGS. 5A-C show steps of a method of fabricating a device according to embodiments.

In some embodiments, the first, second, and third layers of the device may be fabricated into one or more pieces that are then assembled. FIGS. 5A-5C show an example of fabricating and assembly of a device according to embodiments, for example, the device 100.

In some embodiments, a coverslip 510 can be prepared with the pattern of cell interaction regions 544 for a top surface of a hydrogel to form the hydrogel layer 542. In some embodiments, a coverslip (e.g., No 1.5 coverslips 18 mm×18 mm) can be stamped with fibrinogen.

In some embodiments, the coverslip 510 with the cell interaction regions 544 may be prepared using an etched silicon mold. Next, fibrinogen, for example, AF488, can be incubated on PDMS squares (e.g., 10 mm×10 mm×3 mm), for example, at 30 ug/mL for a period of time (e.g., for about 1 hour). The silicon mold, having holes corresponding to the desired pattern of cell interaction regions 544, can be prepared by, for example, cleaning (e.g., for example, ultrasonically in ethanol for about 30 min, rinsed with distilled and deionized (DI) water, dried), and treatment, for example, with an O2 plasma for a period of time (e.g., about 30 s). The PDMS squares can be prepared by, for example, by being rinsed with DI water, air dried, and placed on the silicon mold. After adhering to the mold, the PDMS squares can be removed and placed on coverslips (such as 25 mm), which may have previously been treated with an O2 plasma. Using a silicon mold can provide advantages over other methods, such as PDMS pillars to stamp the coverslip 510, because the silicon based technique can be capable of creating small fibrinogen features with large empty spaces.

In some embodiments, a first layer 532 and a second layer 534 may also be prepared and fabricated for assembly of the device. In some embodiments, the first layer 532 (e.g., bottom coverslip) can be silanized by an O2 plasma treatment, and subsequently treated with an APTMES/Ethanol/Glacial acetic acid solution (e.g., for about 90 min at about 60 C). The first layer 532 can then be removed and rinsed with 70% ethanol/30% DI water and then with DI water. The first layer 532 can then be treated, for example, with a 2% glutaraldehyde solution at room temperature for a period of time (e.g., 30 minutes). The first layer 532 can then be rinsed and dried.

In some embodiments, to fabricate the second layer 534 of the device, long rectangular holes (1 mm×25 mm) can be laser cut into a thin sheet of pre-fabricated PDMS to form channels 530 for the hydrogel 546. Next, the second layer 534 (e.g., PDMS sheet) can be cleaned and covalently bonded to the first layer 532 (e.g., 24×40 mm No. 1 coverslip). In some embodiments, the bonding can be enhanced by applying a heat treatment for a period of time.

In some embodiments, the first step of assembling the device is shown in FIG. 5A. The coverslip 510 with the cell interaction regions 544 can be inverted over the second layer 534 and the first layer 532. Before placing the coverslip 510 stamped with the pattern of cell interaction regions 544, the first layer 532 and the second layer 534 (e.g., corresponds to the second and third layers) can be silanized using the above method. In some embodiments, the silanization may occur after an incubation in DI water after APTES treatment. This water treatment can significantly improve the PDMS flexibility and surface adhesion such that it could create a good seal when pressed against a second coverslip.

In some embodiments, the piece shown in FIG. 5A (i.e., coverslip 510 with the cell interaction regions 544 inverted over the bonded first layer 532 and second layer 534) can be placed in a vacuum. The vacuum can help remove some of the air from the PDMS, which can interfere with hydrogel polymerization.

Next, a hydrogel solution can be injected into the channels 530 created in second layer 534 to form the hydrogels 546 for the hydrogel layer 542, for example, as shown in FIG. 5B. In some embodiments, the hydrogel solution may be a polyacrylamide solution. In some embodiments, the solution for the hydrogel may be a polyacrylamide solution with a ratio of acrylamide to bis-acrylamide specific to the desired stiffness (engler paper), supplemented with phosphate-buffered saline (PBS). In some embodiments, the hydrogel gel 546 can be made from a mixture of a polyacrylamide solution, tetramethylethylenediamine (TMED), ammonium persulfate (APS), and NHS-ester.

To reduce the amount of unpolymerized gel both along the edges of the coverslip and the device (e.g., as shown in FIG. 5B), the hydrogel 546 may be made in an argon glove box.

After injecting the solutions, the hydrogel 546 can polymerize to form the hydrogel layer 542. After polymerization, the top coverslip 510 can be discarded leaving the hydrogel layer 542 (e.g., a hydrogel 546 with a pattern of cell interaction regions 544 on the top surface). In some embodiments, the hydrogel layer 542 can be placed in PBS for a period of time for storage.

Next, as shown in FIG. 5C, the hydrogel layer 542 may be covered with the third layer 536 (e.g., a top layer). In some embodiments, the third layer 536 may be fabricated to have channels 538 that are slightly larger than the hydrogel layer. For example, the third layer 536 may be made by a separate SU-8 mold. The third layer may be attached to the second layer 534 (bonded to the first layer 532) including the hydrogel layer 542 with an adhesive 550. In some embodiments, the adhesive 550 may be a piece of double sided tape that was laser cut with rectangular holes matching that of the third layer 536. In other embodiments, the adhesive 550 can be different. The adhesive 500 can be placed around the hydrogel layer 542, and the second layer 534 can then be pressed onto the adhesive 550.

In some embodiments, the device can be prepared for storage until use by flowing PBS into the enclosed channel.

Figure 6:
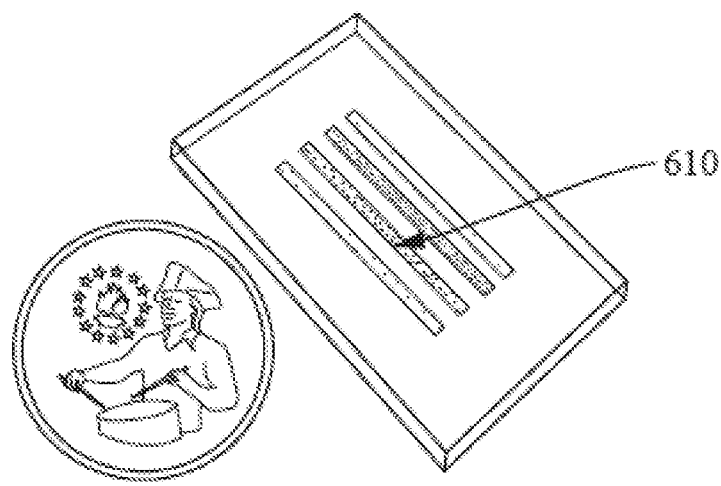
FIG. 6 shows an example of a device according to embodiments.

FIG. 6 shows an example 600 of a device according to embodiments.

It is to be understood that the fabrication of the devices according to embodiments is not limited to the above methods and may be fabricated by other methods. Variety of techniques may be employed to fabricate or manufacture devices of the disclosure, and the technique employed may be selected based in part on the material of choice. For example, materials for the first, second and third layers include any rigid or flexible machinable material, such as glass, co-polymer, polymer or flexible elastomeric material.

The materials may also include but are not limited to silicon, steel, nickel, poly(methylmethacrylate) (PMMA), polycarbonate, polystyrene, polyethylene, polyolefins, silicones (e.g., poly(dimethylsiloxane)), and combinations thereof. The materials may also be any known materials known in the art, such as those commonly used in microfluidic devices. The devices may also be formed according to any known methods in the art. Methods may include photolithography (e.g., stereolithography or x-ray photolithography), molding, embossing, silicon micromachining, wet or dry chemical etching, milling, diamond cutting, Lithographie Galvanoformung and Abformung (LIGA), electroplating, laser micromachining, thermoplastic injection molding, and compression molding.

The devices according to embodiments may be part of a system. In some embodiments, the system may include a property determination device. The property determination device may be a computer having a CPU and memory. The system may also include a microscope configured to analyze the cells with respect to the interaction with the cell interaction regions. For example, the cells can be analyzed by measuring the center to center distance of the cell with respect to the group of cell interaction sites of a cell interaction region.

While the disclosure has been described in detail with reference to exemplary embodiments, those skilled in the art will appreciate that various modifications and substitutions can be made thereto without departing from the spirit and scope of the disclosure as set forth in the appended claims. For example, elements and/or features of different exemplary embodiments may be combined with each other and/or substituted for each other within the scope of this disclosure and appended claims.

The invention claimed is:

1. A device for measuring at least one property of at least one cell, comprising:
    one or more wells, each well including an inlet, an outlet, and a channel disposed between the inlet and the outlet; and
    a hydrogel layer disposed in the channel, the hydrogel layer including a hydrogel having a top surface on which a pattern of cell interaction regions are directly disposed;
    wherein:
        each cell interaction region includes a row of at least a first interaction site and a second interaction site spaced from the first interaction site by a distance;
        the pattern of cell interaction regions includes a plurality of evenly spaced columns;
        the plurality of the evenly spaced columns includes at least a first column of one or more cell interaction regions and a second column of one or more cell interaction regions spaced from the first column by a distance;
        the first column and the second column are disposed directly adjacent to each other;
        the distance between the first column and the second column is greater than distance between the first interaction site and the second interaction site of each cell interaction region; and
        each cell interaction site includes fibrinogen.

2. The device according to claim 1, wherein each cell interaction region has a size that is configured to correspond to a size of at least one cell to be measured.

3. The device according to claim 1, the device further comprising:
    a layer disposed above the hydrogel layer, the layer including the channel configured to receive a sample that includes the at least one cell.

4. The device according to claim 1, further comprising:
    a layer including in which the hydrogel layer is disposed, the hydrogel layer extending above the layer.

5. The device according to claim 1, further comprising:
    a first layer;
    a second layer disposed above the first layer, the hydrogel layer being disposed in the second layer; and
    a third layer, the third layer being disposed above the second layer and the hydrogel layer,
    wherein the channel is configured to receive a sample that includes at least one cell.

6. The device according to claim 1, wherein each well is self-contained.

7. A device for measuring at least one property of a cell, comprising:
    a plurality of wells, each well including:
        an inlet, an outlet, and a channel disposed between the inlet and the outlet; and
        a hydrogel layer disposed in the channel, the hydrogel layer including a hydrogel having a top surface on which a pattern of cell interaction regions are directly disposed;
    wherein:
        each cell interaction region includes a row of at least a first interaction site and a second interaction site spaced from the first interaction site by a distance;
        the pattern of cell interaction regions includes a plurality of evenly spaced columns;
        the plurality of the evenly spaced columns includes at least a first column of one or more cell interaction regions and a second column of one or more cell interaction regions spaced from the first column by a distance;
        the first column and the second column are disposed directly adjacent to each other;
        the distance between the first column and the second column is greater than distance between the first interaction site and the second interaction site of each cell interaction region;
        each well includes a different biochemical condition and/or hydrogel layer; and
        each cell interaction site includes fibrinogen.

8. The device according to claim 7, wherein each well includes a different hydrogel, a different pattern of cell interaction regions, a different biochemical condition, or a combination thereof.

9. The device according to claim 7, wherein each well includes a hydrogel with a different stiffness.

10. The device according to claim 7, further comprising:
    a first layer;
    a second layer disposed above the first layer, the hydrogel layer being disposed in the second layer; and
    a third layer, the third layer being disposed above the second layer and the hydrogel layer,
    wherein the channel is configured to receive a sample that includes at least one cell.

11. The device according to claim 7, wherein each well includes a different hydrogel, each hydrogel having a different ratio of acrylamide to bis-acrylamide.

* * * * *